United States Patent [19]

Smith et al.

[11] Patent Number: 5,770,160
[45] Date of Patent: Jun. 23, 1998

[54] POSITIVE DISPLACEMENT LIQUID DRAWING AND DISPENSING APPARATUS

[75] Inventors: James C. Smith, Hayward; Donald H. DeVaughn, San Francisco, both of Calif.

[73] Assignee: Bio-Plas, Inc., San Francisco, Calif.

[21] Appl. No.: 906,137

[22] Filed: Jul. 25, 1997

Related U.S. Application Data

[63] Continuation of Ser. No. 528,780, Sep. 15, 1995, abandoned.
[51] Int. Cl.[6] .................................. B01L 3/02; G01N 1/14
[52] U.S. Cl. ...................... 422/100; 422/103; 422/104; 73/864.13; 73/864.14; 436/180
[58] Field of Search ..................................... 422/100, 101, 422/103, 104; 436/180; 73/864.01, 864.13, 864.14, 864.16, 864.34, 864.51, 864.63

[56] References Cited

U.S. PATENT DOCUMENTS

| | | | |
|---|---|---|---|
| 3,525,264 | 8/1970 | Nieglos et al. | 73/425.6 |
| 3,965,750 | 6/1976 | Johnson | 73/864.01 |
| 4,197,735 | 4/1980 | Munzer et al. | 73/61.4 |
| 4,487,081 | 12/1984 | De Vaughn et al. | 73/864.13 |
| 5,192,511 | 3/1993 | Roach | 422/100 |
| 5,449,494 | 9/1995 | Seeney | 422/100 |
| 5,465,768 | 11/1995 | DeRoos et al. | 73/864.63 X |

Primary Examiner—Harold Y. Pyon
Attorney, Agent, or Firm—Flehr Hohbach Test Albritton & Herbert

[57] ABSTRACT

A positive displacement liquid drawing and dispensing apparatus (21) having a tubular member (22) with an axially extending lumen (24) and a plunger (31) mounted for axial displacement in the lumen (24). The plunger (31) has a first seal (33) positioned proximate an end (34) of the plunger and a second seal (37) axially spaced from the first seal (33). The first and second seal each slidably and sealingly engage an interior surface (23) defining the lumen (24) as the plunger (31) is displaced in the lumen. The plunger further includes a recess (38) intermediate the first and second seals for receipt of trapped gas (40,41) which can be drawn in through an intake end (27) of the lumen during drawing of the liquid (36) into the tubular member (22). The plunger is formed for positioning of the first seal (33) beyond the intake opening (27) so that air will automatically be isolated between the first and second seals (33,37) as the plunger is withdrawn into a lumen. A substantially gas-free draw of liquid will result between the first seal (33) and the intake opening (27). A method of drawing the liquid in the apparatus which includes automatically isolating an uppermost portion of the liquid (36) and gas (41) from a lower portion of the volume drawn into the apparatus (21).

20 Claims, 3 Drawing Sheets

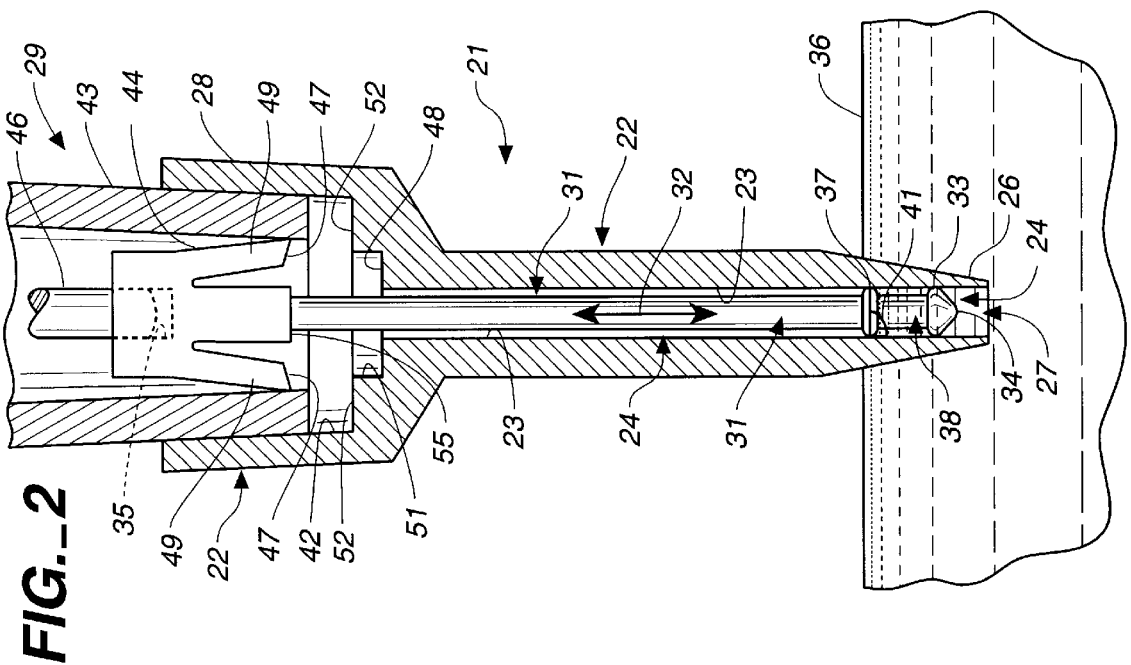
FIG._1
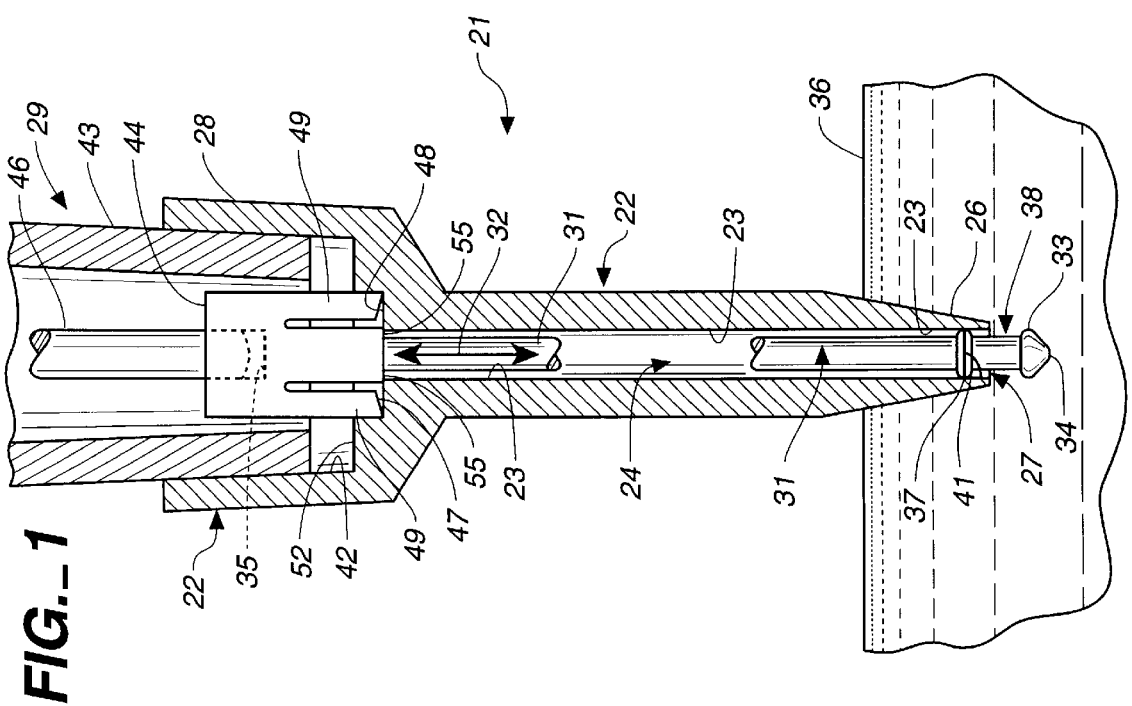
FIG._2

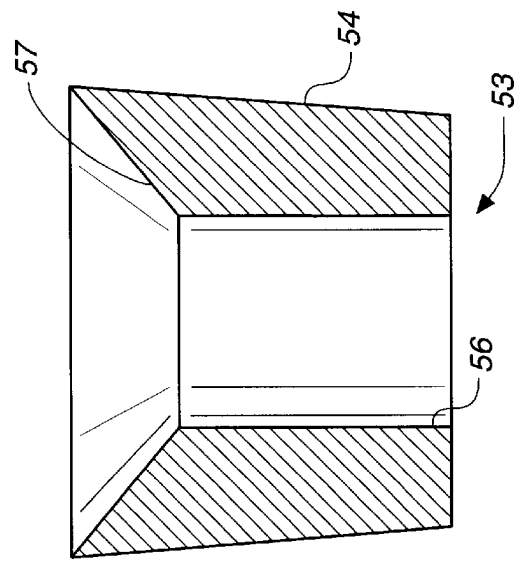
FIG._5
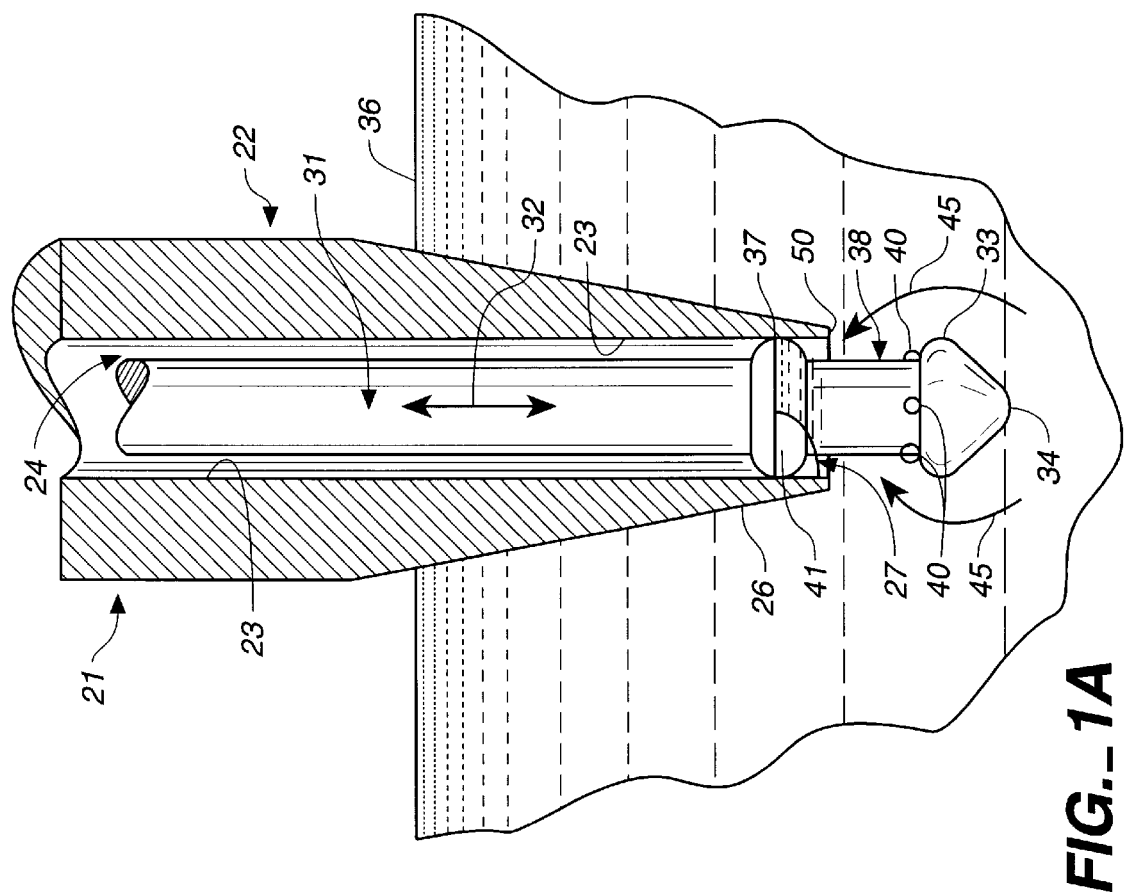
FIG._1A

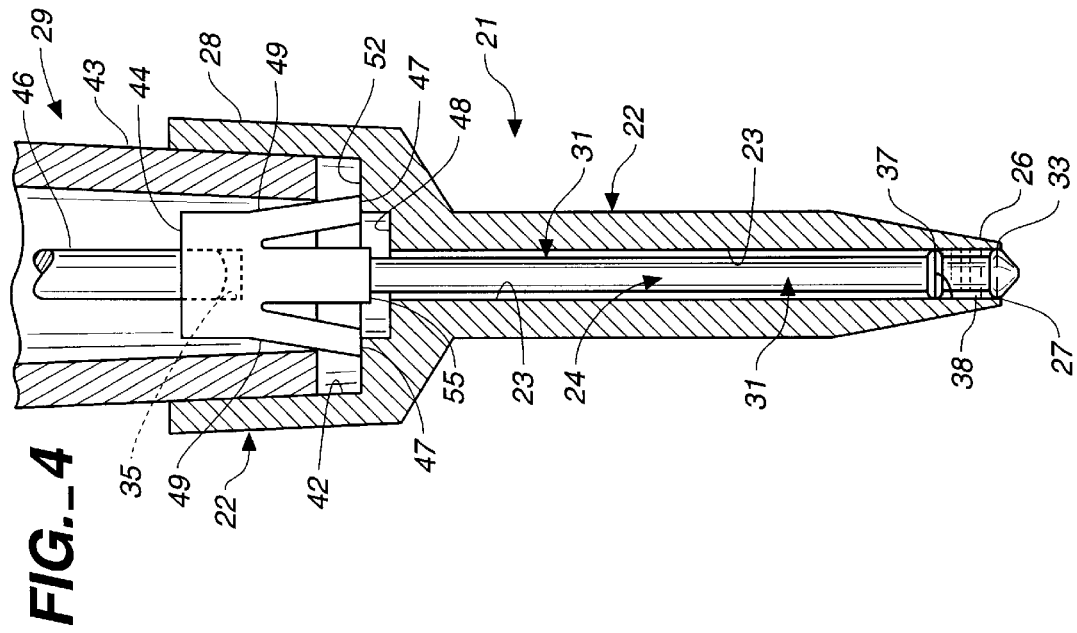
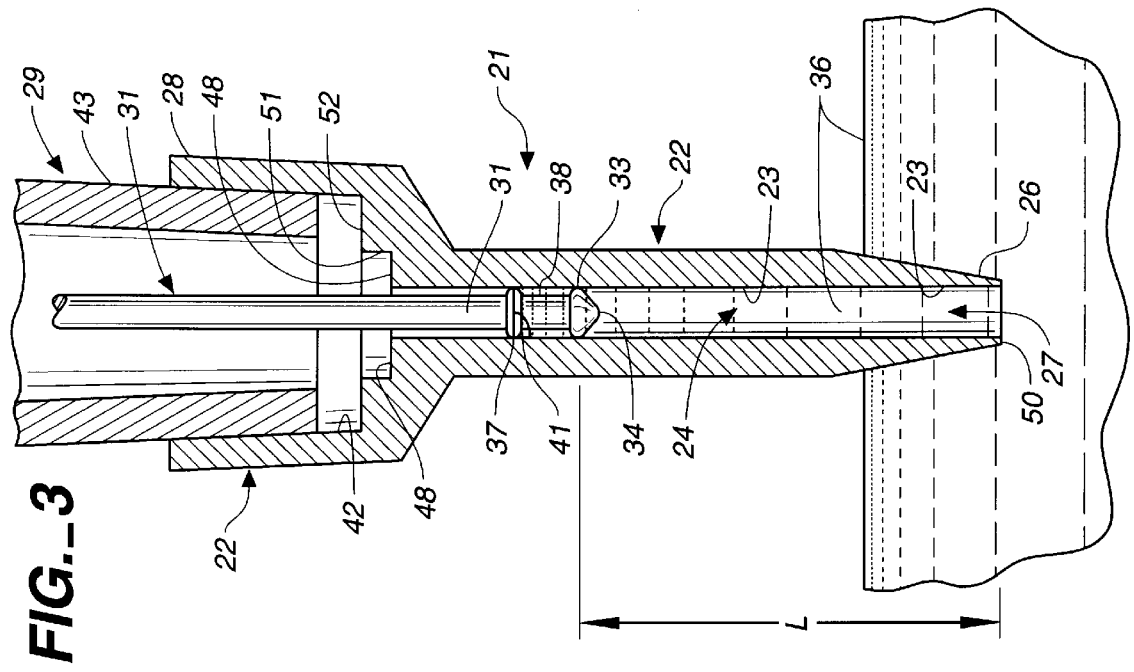

POSITIVE DISPLACEMENT LIQUID DRAWING AND DISPENSING APPARATUS

This is a continuation of application Ser. No. 08/528,780 filed Sep. 15, 1995 now abandoned.

TECHNICAL FIELD

The present invention relates, in general, to liquid drawing and dispensing apparatus, and more particularly, relates to positive displacement apparatus, such as pipette tips and syringes, in which a plunger or piston is provided that is displaccable in order to draw and dispense precise volumes of liquids.

BACKGROUND ART

Positive displacement pipette tips have been widely used in the medical industry for many years. Such apparatus are used to draw, transport and dispense very accurate volumes of liquids as part of scientific and medical experiments and treatment regimes.

Such positive displacement liquid drawing and dispensing apparatus typically include a tubular barrel having a lumen which is calibrated to have a known volume so that precise liquid volumes can be drawn and dispensed. A plunger or piston is slidably mounted in the lumen, and as the piston is withdrawn from an intake aperture of the tip, fluid is drawn into the lumen. On the reverse stroke of the plunger or piston, the liquid is dispensed. The system is characterized as a positive displacement system in that once the intake end of the tubular member is immersed in the liquid to be drawn, displacement of the piston effects a very positive and reproducible intake or draw of the liquid. Similarly, piston movement in the opposite direction positively displaces and dispenses the liquid from the apparatus. By comparison, in non-positive pipette tip systems there exists an air cushion between the pipetter and the pipette tip so that displacement of liquid in and out of the tip is not as reproducible or precise.

A problem which has been encountered in connection with positive displacement pipette tips is that air, either trapped between the end of the pipette tip and the liquid to be drawn, or trapped in the apparatus itself as a result of lack of wetting of the components, will be drawn into the lumen with the liquid so that a gas bubble exists in the lumen with the drawn liquid. While this bubble is normally quite small, it nevertheless affects the volume of liquid drawn and dispensed. As the liquid volume to be drawn becomes smaller, the volume of the bubble proportionately affects precision to a greater degree.

Various strategies have been employed to eliminate or reduce the amount of air trapped and drawn into positive displacement pipetters. One technique is to attempt to pre-wet the piston or plunger by drawing liquid in and then expelling it out of the pipette tip. This eliminates or reduces the air between the plunger and barrel by wetting the respective surfaces. This approach can be effective, but it requires the technician to spend more time for each draw and dispensing cycle, which is particularly tedious when hundreds or thousands of cycles must be performed, with a new pipette tip being used for each draw and dispense cycle. In many medical and scientific applications, the tips must be changed for each draw to avoid cross-contamination. Moreover, it is also possible, particularly under the press of time, to insert, even a wetted pipette tip, into the liquid in a manner trapping an air bubble between the liquid and tip end.

Another approach to elimination of the air bubble trapped in a positive displacement pipette tip is to invert the tip and allow the trapped bubble to migrate to proximate the discharge end. Then, a small amount of liquid and the bubble can be discharged while the apparatus is inverted to leave substantially air-free liquid in the lumen of the apparatus. Thereafter, the tip can be used to dispense only liquid from the lumen.

This "solution" to elimination of trapped air from the drawing and dispensing apparatus is similarly very tedious, and it is not well suited for use with pipetters having calibrated piston or plunger displacement. The process of purging the trapped air eliminates an unpredictable volume of the liquid, and the volume of liquid remaining in the apparatus, therefore, can vary, which is acceptable for dispensing volumes which need only be checked by visual observation, but is less acceptable for pipetting applications in which extremely small and precise volumes of liquids must be automatically dispensed.

DISCLOSURE OF INVENTION

Accordingly, it is an object of the present invention to provide a positive displacement liquid drawing and dispensing apparatus having improved accuracy and ease of use.

It is a further object of the present invention to provide a positive displacement liquid drawing and dispensing apparatus and method in which air trapped, between the liquid and the apparatus, or between the components of the apparatus will not influence the precision of the volume of liquid drawn and dispensed.

Still a further object of the present invention is to provide a positive displacement pipette tip and method for use of the same in which pre-wetting and purging are not required and air inherently present can be drawn into the tip and isolated from the liquid drawn into the tip.

Another object of the present invention is to provide a positive displacement pipette tip which is easy and inexpensive to construct, is easy to use and is adaptable to a wide range of applications.

The apparatus and method of the present invention have other objects and features of advantage which will become apparent from, and are set forth in more detail in, the following Best Mode of Carrying Out the Invention and accompanying drawing.

The liquid drawing and dispensing apparatus of the present invention is comprised, briefly, of a tubular member having an interior surface defining an axially extending lumen terminating in an opening enabling drawing of liquid into the lumen, and a plunger mounted for axial displacement in the lumen and having a first seal positioned proximate an end of the plunger closest to the opening and a second seal positioned axially spaced from the first seal. The first seal and second seal each slidably and sealingly engage the interior surface defining the lumen as the plunger is displaced in the lumen, and the plunger is recessed intermediate the first seal and second seal for receipt of gas or air trapped during drawing of the liquid into the apparatus. The plunger is further formed for positioning of the first seal and recess outwardly of the intake opening of the tubular member so that air trapped between the components or under the plunger can communicate with the recess and automatically will be isolated between the first seal and the second seal as the plunger is withdrawn inwardly into the lumen. The plunger is further mounted for displacement inwardly displaced until the first seal is at a predetermined known distance from the aperture so that a calibrated, substantially gas-free, volume of liquid is drawn into the lumen between the first seal and the intake opening.

The method of drawing a substantially gas-free volume of liquid into a liquid drawing and dispensing apparatus of the present invention is comprised, briefly, of the steps of placing an intake opening of the apparatus in the liquid to be drawn, drawing a volume of the liquid and any gas trapped proximate the intake opening into the apparatus, and during the drawing step, isolating an uppermost portion of the volume drawn into the apparatus, including substantially all of the trapped gas, from a remainder portion of the volume, whereby the remainder portion of the volume drawn into the apparatus is substantially gas-free. The isolating step is preferably accomplished by sealing the uppermost portion of the volume from the remainder portion of the volume by employing a movable plunger having two seals and displacing the plunger from a first position, in which one seal is outwardly of the intake opening, to a second position, in which the first seal has been moved inwardly of the intake opening to trap the gas between the first and second seal. The method further includes the step of dispensing the remainder, gas-free portion of the volume drawn from the apparatus without dispensing the uppermost portion containing the trapped gas or air.

BRIEF DESCRIPTION OF THE DRAWING

FIG. 1 is a fragmentary, side elevation view of a positive displacement pipette tip constructed in accordance with the present invention and mounted on the end of a pipetter with the tip plunger in a position to start a liquid draw.

FIG. 1A is an enlarged, fragmentary, side elevation view of the pipette tip of FIG. 1.

FIG. 2 is a side elevation view corresponding to FIG. 1 with the plunger in an intermediate position during the draw.

FIG. 3 is a side elevation view corresponding to FIG. 1 with the pipette tip plunger in a position at the end of the draw.

FIG. 4 is a side elevation view corresponding to FIG. 1 in which the pipette tip is shown in a position at the end of a dispensing stroke.

FIG. 5 is a side elevation view of a tool or sleeve which may be used to mount the pipette tip plunger in its receiving tip body.

BEST MODE OF CARRYING OUT THE INVENTION

The positive displacement liquid drawing and dispensing apparatus of the present invention can best be illustrated by describing a pipette tip constructed in accordance with the present invention. It will be understood, however, that other positive displacement liquid drawing and dispensing apparatus, such as syringes, can be constructed in an analogous manner.

Referring now to FIGS. 1 and 1A, the positive displacement liquid drawing and dispensing apparatus of the present invention, generally designated 21, can be seen to be comprised of a tubular member, generally designated 22, having an interior surface 23 which defines an axially extending lumen 24. One end 26 of tubular tip 22 is formed with an opening or aperture 27 which communicates with lumen 24, while an opposite end 28 of tubular member 22 can be formed for coupling to an actuator, such as a pipetter, generally designated 29.

In order to provide a positive draw and dispensing system, apparatus 21 of the present invention preferably further includes a plunger or piston, generally designated 31, which is mounted for axial reciprocation or displacement in lumen 24, as indicated by arrows 32. In prior art positive displacement pipette tips, plunger or piston 31 typically will include a seal assembly, such as first seal assembly 33, which is formed proximate the end 34 of plunger 31 and which slidably and sealingly engages interior surface 23 defining lumen 24. As the plunger is moved away from intake opening or aperture 27, therefore, the first seal 33 will draw liquid 36 up into lumen 24, for example as shown in FIGS. 2 and 3.

In the improved positive displacement pipette tip of the present invention, however, a second seal 37 is provided on plunger or piston 31 in axially spaced relation to first seal 33. The second seal 37 similarly slidably and sealingly engages interior surface 23 defining lumen 24. Moreover, in order to automatically isolate air, or other gas, from the liquid drawn into the pipette tip of the present invention, plunger 31 further includes or is formed with a recess 38 intermediate first seal 33 and second seal 37. Recess 38 traps air or gas during the liquid draw, in a manner which will be described in more detail hereinafter.

Most positive displacement pipette tips are formed of injection molded thermoplastic materials, such as polyethylene or polypropylene, which is not easily wetted by many liquids. Accordingly, when draw end 26 of the tip is placed in a liquid 36, a gas (in most cases air) will be trapped between the liquid to be drawn and the various components of the pipette tip, namely, the tubular barrel 22 and plunger 31. In prior art tips techniques such as pre-wetting the components, and/or drawing, inverting and dispensing any trapped air, have been used to try to obtain air or gas-free liquid draws. In the present invention, the dual seal assembly 33 and 37 automatically isolates any trapped air from a drawn volume of substantially air or gas-free liquid.

In FIG. 1A, it will be seen that first seal 33 is in a first position in which the first seal is positioned outwardly of aperture 27. The plunger assembly 31 of the resent invention, therefore, must also be formed so that he first seal can be positioned in a first position outwardly of aperture 27. It will also be seen that in this first position of FIG. 1A, recess 38 between the first seal 33 and second seal 37 is in communication with liquid 36, and second seal 37 is still in sliding sealed engagement with surface 23 of lumen 24. The first position of plunger 31, as shown in FIG. 1A, results in the wetting of most of the plunger end and most of the plunger between the first seal and second seal. Any air trapped beneath the end of the tip, or in lumen 24 between the plunger and barrel 22, will form bubbles 40 and 41, which will migrate due to buoyancy and/or liquid intake, as indicated by arrows 45, to the position of bubble 41 next to second seal 37. Accordingly, in the positive displacement tip of the present invention no effort is made to avoid formation of bubbles 40 and 41 inside the end of lumen 24. Instead, bubbles 40 and 41 are tolerated and merely allowed to rise up and collect against second seal 37.

Plunger 31 is now displaced in an upward direction to withdraw first seal into lumen 24 through aperture 27. FIG. 2 illustrates the position of the plunger shortly after the same has been drawn into the lumen. As will be seen from FIG. 2, recess 38 is now filled with some liquid 36 and at least one bubble 41 proximate seal 37. Below first seal 33, however, lumen 24 is filled with substantially gas-free liquid. The trapped air or gas 41. is isolated between the first seal and second seal in recess 38 so that below or outwardly in lumen 24 of first seal 33 the liquid does not contain air bubbles.

As shown in FIG. 3, plunger 31 is displaced further inwardly from aperture 27 to a second position at which first seal 33 is inwardly of aperture 27 by a predetermined stroke length L. Since lumen 24 has a known diameter, which may or may not taper, the precise volume contained between aperture 27 and first seal 33 after stroke L will be known, and that volume will be filled with the gas-free liquid to be dispensed. It will be seen in FIG. 3 that bubble 41 remains isolated or sealed between first seal 33 and second seal 37 in a volume above the volume of stroke L.

Thus, during the draw process using the tip assembly of the present invention a volume of liquid and air is drawn into lumen 24, and the double seal 33/37 isolates an upper most portion of this volume in recess 38. This uppermost portion of the volume drawn in contains all of the air, namely, bubble 41, while a remainder portion of the volume drawn in, namely, the portion between seal 33 and aperture 27, is substantially air or gas-free.

Next, as shown in FIG. 4, plunger or piston 31 is displaced downwardly or toward aperture 27 until first seal 33 reaches a third position, namely, a position at which first seal 33 is substantially exactly at aperture 27. In this third position, however, first seal 33 still remains in sealed relation to surface 23 at aperture 27 so that any liquid between first seal 33 and second seal 37 is not dispensed, and bubble 41 remains isolated between the first and second seals so that it similarly is not dispensed. The result is that all of the liquid in lumen 24 over stroke length L, is dispensed by plunger 31. Hence, a very precise and reproducible volume can be dispensed by pipette tip assembly 21 without pre-wetting or purging. The pipette tip of the present invention, therefore, allows the technician to merely insert tip end 26 in liquid 36 with the plunger 31 in the first position, draw the plunger to the second position to automatically isolate any trapped air or bubbles 40, 41, remove the tip from the liquid, and thereafter dispense a very precise volume of liquid from the tip. This can be accomplished without tedious or time consuming tip manipulation techniques which require care and technician skill.

Now returning again to FIG. 1, some further details of the positive displacement pipette tip of the present invention can be described. In the preferred form, tip assembly 21 is formed with an upper end 28 that has a slightly tapered socket portion 42 which will slidably receive and frictionally retain a tapered mating end 43 of an actuator assembly, such as pipetter 29. The upper end 44 of plunger 31 can be formed for coupling to the plunger or piston 46 of pipetter 29, for example, by being formed with a bore or slot 35 dimensioned to receive the end of pipetter piston 46 in a press fit relationship in the bore. As shown in FIGS. 1 and 2, slot 35 is dimensioned relatively deep to enable adjustment of the tip of piston 46 in the slot, depending upon how hard the user engages the pipette tip.

Indexing of plunger 31 in the first position of FIGS. 1 and 1A can be accomplished by seating of downwardly facing shoulder 55 on upper end 44 of the plunger 31 with upwardly facing shoulders 48 of tip socket end 28. Thus, pipetter piston 46 can be press fit into bore or slot 35 in pipette tip end 44 to virtually any depth which will cause the assembly to move as a unit without changing the ability to index or move tip end 34 to the proper first position, which is controlled by interengagement of shoulders 55 and 48.

In order to control indexing of first seal 33 in the dispensing or third position of FIG. 4, it is preferable that upper end 44 of plunger 31 also be formed with at least one resiliently outwardly biased wing 49, and preferably a wing 49 on each side of plunger upper end 44. As will be seen by comparing FIGS. 2 and 4, wings 49 are initially captured in socket 51 (FIGS. 1 and 2) in the upper end 28 of the pipette tip. As plunger 31 is withdrawn past upwardly facing shoulders 52, wings 49 are free to spring outwardly. At the end of the return or dispensing stroke, ends or wing shoulders 47 on wings 49 now engage upwardly facing shoulders 52 and prevent further downward displacement of plunger 31 just as seal 33 reaches the third position at which dispensing of liquid is to be terminated. In the preferred form, wing shoulders 47 are tapered in a manner so that upon resilient extension of wings 49, wing shoulder 47 will flushly engage shoulder 52 (FIG. 4).

Initial placement of upper plunger end 44 and wings 49 in receiving socket 51 can be accomplished at the factory or by the user using a removable tool or adaptor sleeve 53 having an outside diameter 54 equal to the diameter of socket 42 and a bore 56 with the diameter of socket 51. The upper or entrance end of the tool can be tapered at 57 so that insertion of wings 49 down into tool 53 will automatically close wings 49 to socket size 51 so as to allow insertion of collapsed wings 49 into socket 51 to the position shown in FIG. 1. Tool 53 could then be removed and pipetter plunger 46 press fit into the bore in upper end 44 of plunger 31. Resilient outward biasing of wings 49 can be accomplished by molding them in the position of FIGS. 2 and 4 and then collapsing them against the inherent memory of the plastic.

Pipetters are well known in the industry today which include a stroke sequence substantially as follows. First, the pipetter actuator or plunger 46 can be advanced from a start position to a first stop, which can correspond to the first position as shown in FIG. 1. The tip can then be immersed in the specimen or sample and the pipetter actuator or plunger 46 returned to the start position, which can be the second tip position as shown in FIG. 3. The tip is then removed from the sample or specimen, and the meniscus at aperture 27 minimized by wiping or shaking the tip slightly. Next, the tip is placed over the receiving vessel (not shown) and the pipetter depressed so as to move actuator 46 down to a stop position just short of the initial stop position, namely, the third position shown in FIG. 4. This requires that the pipetter 29 be set up so that the dispensing stroke is slightly shorter than the draw stroke in order that first seal 33 is not advanced beyond aperture 27. In the illustrated tip, wings 49 act as a stop which prevents advancing past the third position.

It also is possible to eliminate wings 49 and employ a pipetter in which the stroke length is adjustable. Pipetters, for example as manufactured and sold by Bio-Plas, Inc. Of San Francisco, Calif., are readily adjustable to provide the necessary stroke sequence for use with the pipette tip of the present invention. Pipetters by other manufacturers also can be adapted to shorten the dispensing stroke, as compared to the draw stroke. For example, although not automatic, one can shorten the stroke length after the draw and before dispensing. The tip shown in the drawing, however, can be used with pipetters which do not permit ready adjustment of the stroke length to produce the difference between the draw and dispense strokes.

In the pipette tip of the present invention, first seal 33 preferably is positioned substantially at distal end 34 of plunger 31, and the plunger is convergently tapered at distal end 34 in an outward direction. Tapered plunger end 34 facilitates passage of any trapped air bubbles underneath seal 33 into recess 38 between the two seals. This ensures that air bubbles are not retained outwardly of first seal 33, but instead are isolated between first seal 33 and second seal 37. As will be appreciated, the volume of tapered end 34 must be considered when calibrating the liquid volume inside lumen 24 over stroke length L if the tapered end extends into the liquid volume to be dispensed. If the third position stops inwardly of the tip end 27, which is also possible, then the volume dispensed will not be affected by tapered end 34 of the plunger.

It is further preferable that seals 33 and 37 are formed by annular protrusions extending transversely from the sides of plunger 31 to engage interior surface 23. Most preferably, lumen 24 is cylindrical, as is the rod-like plunger or piston 31. The piston 31 has a diameter less than lumen 24 and the annular protrusions 33 and 37 can advantageously be formed as O-ring-like members, preferably integrally formed during injection molding with rod-like piston 31. The recess 38 is provided by an extension of the reduced diameter of the rod-like piston 31, and seals 33, 37, surface 23 and the rod-like piston 31 define the recess volume 38 in which bubbles 40 and 41 are isolated.

It is also advantageous that the exterior surface of tip end 26 of pipette tip taper convergently inwardly toward aperture 27 so as to define an annular edge 51 which is very thin or knife-like and small an area relative to aperture 27. The knife edge 58 reduces the possibility of air being trapped or caught on knife edge surface 58 and then drawn into lumen 24 after seal 33 enters aperture 27.

As will be apparent from the above description of the apparatus of the present invention, the method of drawing a substantially gas-free volume of liquid into a positive displacement pipette tip of the present invention includes the steps of immersing intake opening 27 of tip 21 in liquid 36, drawing a volume of the liquid and any gas 41 trapped proximate intake opening 27 into the apparatus, and during the drawing step, isolating an uppermost portion of the volume drawn into the apparatus, including substantially all of the gas in the form of bubble 41, from a remainder of the volume, whereby liquid 36 below seal 31 in this remainder volume is substantially gas-free. The isolating step is accomplished by sealing the uppermost portion of the volume drawn into the apparatus from the remainder portion of the volume by moving a double or dual seal assembly in the apparatus from a position allowing the gas to enter a recess between the two seals to a position trapping the air or gas between the two seals. The method of the present invention further preferably includes continuing the draw step until the remainder volume equals a precise amount, for example, a stroke distance L, which is known for a known lumen diameter. Finally, the method of the present invention includes, after the drawing step, the step of dispensing the remainder portion of the volume drawn into the pipette tip.

What is claimed is:

1. A liquid drawing and dispensing apparatus comprising:
   a tubular member having an interior surface defining an axially extending lumen having a length dimension and terminating in a draw opening enabling drawing of a liquid into said lumen and dispensing of liquid therefrom; and
   a plunger mounted for axially displacement in said lumen in a first direction to draw liquid into said lumen and a second opposite direction to dispense liquid from said lumen, said plunger having a length dimension extending over substantially the entire length dimension of said lumen, said plunger having a first seal positioned proximate a draw end of said plunger closest to said draw opening and a second seal positioned axially spaced from said first seal in a direction away from said draw end, said first seal and said second seal each slidably and sealingly engaging said interior surface as said plunger is displaced axially in said lumen, and said plunger being recessed intermediate said first seal and said second seal for receipt of gas trapped during drawing in of said liquid, and said plunger having a length dimension sufficient for displacement of said first seal to a position outwardly of said draw opening while said plunger is coupled to a pipetter, and said first seal is dimensioned to be drawn back into said lumen through said draw opening during drawing of liquid.

2. The apparatus as defined in claim 1 wherein, said lumen has known volume over a predetermined length.

3. The apparatus as defined in claim 1 wherein, said tubular member is a pipette tip having an end opposite said opening formed for mounting to a pipetter; and said opening is formed for drawing liquid into and for dispensing liquid out of said pipette tip.

4. The apparatus as defined in claim 1 wherein, said first seal is positioned proximate a distal end of said plunger and said plunger is convergently tapered outwardly of said first seal.

5. The apparatus as defined in claim 1 wherein, said tubular member is formed with a convergently tapered exterior wall tapering inwardly to said opening and terminating in an annular edge having an area substantially less than the area of said opening.

6. The apparatus of claim 1 and further comprising indexing means for indexing said plunger in a first plunger position wherein said first seal and a portion of said recess are positioned axially beyond said opening and a second plunger positioned wherein said first seal is positioned proximate said opening and said recess is sealed by said first seal within said lumen.

7. The apparatus as defined in claim 1, and a plunger actuator assembly coupled to said plunger for control of axial displacement of said plunger in said lumen.

8. The apparatus as defined in claim 7 wherein, said plunger actuator assembly is formed for displacement of said plunger from:
   a first position, with said first seal and a portion of said recess positioned axial beyond said opening and said second seal positioned axially inwardly of said opening, to:
   a second position with said first seal positioned a predetermined distance axially inwardly of said opening, to draw liquid into said lumen; and
   said plunger actuator assembly is further formed for displacement of said plunger from said second position to:
   a third position with said first seal positioned proximate said opening and said recess sealed by said first seal inwardly of said opening to dispense liquid from said lumen.

9. The apparatus as defined in claim 8 wherein, said tubular member and said plunger are formed for cooperative interengagement to position said first seal in said first position at a start of liquid intake and to limit travel of said first seal past said third position at the end of liquid dispensing.

10. The apparatus as defined in claim 9 wherein, said plunger includes resiliently outwardly displaceable wings, and said tubular member includes shoulders positioned to engage said wings in said first position and said second position to limit travel of said plunger relative to said tubular member.

11. The apparatus as defined in claim 1 wherein,
said first seal and said second seal are formed by annular protrusions extending transversely from sides of said plunger to engage said interior surface.

12. The apparatus as defined in claim 11 wherein,
said lumen is cylindrical;
said plunger is a cylindrical rod having a diameter less than the diameter of said lumen;
said annular protrusions providing said first seal and said second seal are dimensioned for interference fit with said lumen and converge in cross section in a direction toward said interior surface.

13. The apparatus as defined in claim 12 wherein,
said tubular member and said plunger are each formed of injection molded thermoplastic materials.

14. A positive displacement pipette tip assembly for use with a pipetter comprising:
a pipette tip formed with a lumen to receive a liquid therein, said pipette tip having a first end for attachment to a pipetter and a second end with a draw opening therethrough communicating with said lumen to permit the passage of liquid into and from said lumen, and said lumen having a length dimension; and
a plunger displaceably mounted in and extending substantially over said length dimension of said lumen for drawing liquid into said pipette tip and dispensing liquid therefrom, said plunger having a first seal and a second seal axially spaced from said first seal and with each of said first seal and said second seal being dimensioned to slidably engage an inside surface of said pipette tip defining said lumen, said plunger intermediate said first seal and said second seal being formed to receive air trapped above the liquid during drawing of said liquid into said lumen and to isolate said air between said first seal and said second seal from liquid drawn into said lumen outwardly of said first seal,
said plunger having a length sufficient to position said first seal outwardly of said draw opening from a position outside said draw opening, and said first seal being dimensioned to be drawn back into said lumen through said draw opening during drawing of liquid into said lumen.

15. The positive displacement pipette tip as defined in claim 14 wherein,
said lumen has a known volume for a predetermined axial length from said aperture.

16. The apparatus of claim 14 wherein, the plunger, the first seal, and the second seal, are a one-piece component.

17. The positive displacement pipette tip as defined in claim 14 wherein,
said first seal and said second seal are each provided by O-ring protrusions from said plunger, and
said protrusions and said plunger define a volume therebetween to receive and isolate said air.

18. The positive displacement pipette tip as defined in claim 17 wherein,
said first seal is located at a distal end of said plunger and said distal end of said plunger extends outwardly while tapering inwardly from said first seal.

19. The positive displacement pipette tip as defined in claim 14 wherein,
said pipette tip is mounted to a pipetter assembly, and
said pipetter assembly includes an actuator coupled to said plunger for displacement thereof.

20. The positive displacement pipette tip as defined in claim 19 wherein,
said actuator assembly is formed for displacement of said plunger to a first position, at which said first seal and said plunger intermediate said first seal and said second seal are beyond said aperture, and from said first position to a second position, at which said first seal is displaced inwardly of said aperture by a known amount, and from said second position to a third position, at which said first seal is at said aperture and air isolated between said first seal and said second seal remains sealed in said lumen.

* * * * *

UNITED STATES PATENT AND TRADEMARK OFFICE
CERTIFICATE OF CORRECTION

PATENT NO. : 5,770,160
DATED : June 23, 1998
INVENTOR(S) : James C. Smith and Donald H. DeVaughn It is certified that error appears in the above-indentified patent and that said Letters Patent is hereby corrected as shown below:

Column 7, line 20, delete "51" and insert --58--; and

IN THE DRAWINGS:

Figs. 1A and 3, delete reference numeral "50" and insert --58--.

Signed and Sealed this

Tenth Day of November 1998

BRUCE LEHMAN

Attest:

*Attesting Officer*    *Commissioner of Patents and Trademarks*